United States Patent [19]

Fink

[11] 4,182,157
[45] Jan. 8, 1980

[54] SOIL PERCOLATION TESTING APPARATUS

[76] Inventor: Richard E. Fink, R.D. #2, Etters, Pa. 17319

[21] Appl. No.: 887,488

[22] Filed: Mar. 17, 1978

[51] Int. Cl.² .................................................. G01F 23/08
[52] U.S. Cl. ........................................... 73/38; 73/73; 73/322; 116/228
[58] Field of Search ................ 73/38, 73, 322, 319, 73/305; 116/228

[56] References Cited

U.S. PATENT DOCUMENTS

| | | | |
|---|---|---|---|
| 1,267,061 | 5/1918 | DeMeyer | 73/319 |
| 2,266,391 | 12/1941 | Collet | 73/319 |
| 3,099,159 | 7/1963 | Schroeder | 73/322 |
| 3,483,656 | 12/1969 | Baumann | 73/322 X |
| 3,892,126 | 7/1975 | Curtin | 73/38 |
| 3,926,143 | 12/1975 | Hothan | 73/73 X |
| 3,945,247 | 3/1976 | Anderson | 73/73 |
| 3,954,612 | 5/1976 | Wilkerson | 73/305 X |

Primary Examiner—Gerald Goldberg
Assistant Examiner—Joseph W. Roskos
Attorney, Agent, or Firm—C. Hercus Just

[57] ABSTRACT

Percolation testing apparatus comprising an elongated guide rod having one end to be driven into the bottom of a test hole for simple and sole support of the rod along which a gauge rod is slidable by means of guide brackets on the latter and a scale strip is attached to the upper end of said gauge rod for vertical movement relative to a reference marker supported adjustably upon the upper portion of said guide rod. A float is connected to the lower end of the gauge rod for floating movement vertically in the test hole to move the scale strip relative to the reference marker which is stationary on the guide rod.

5 Claims, 7 Drawing Figures

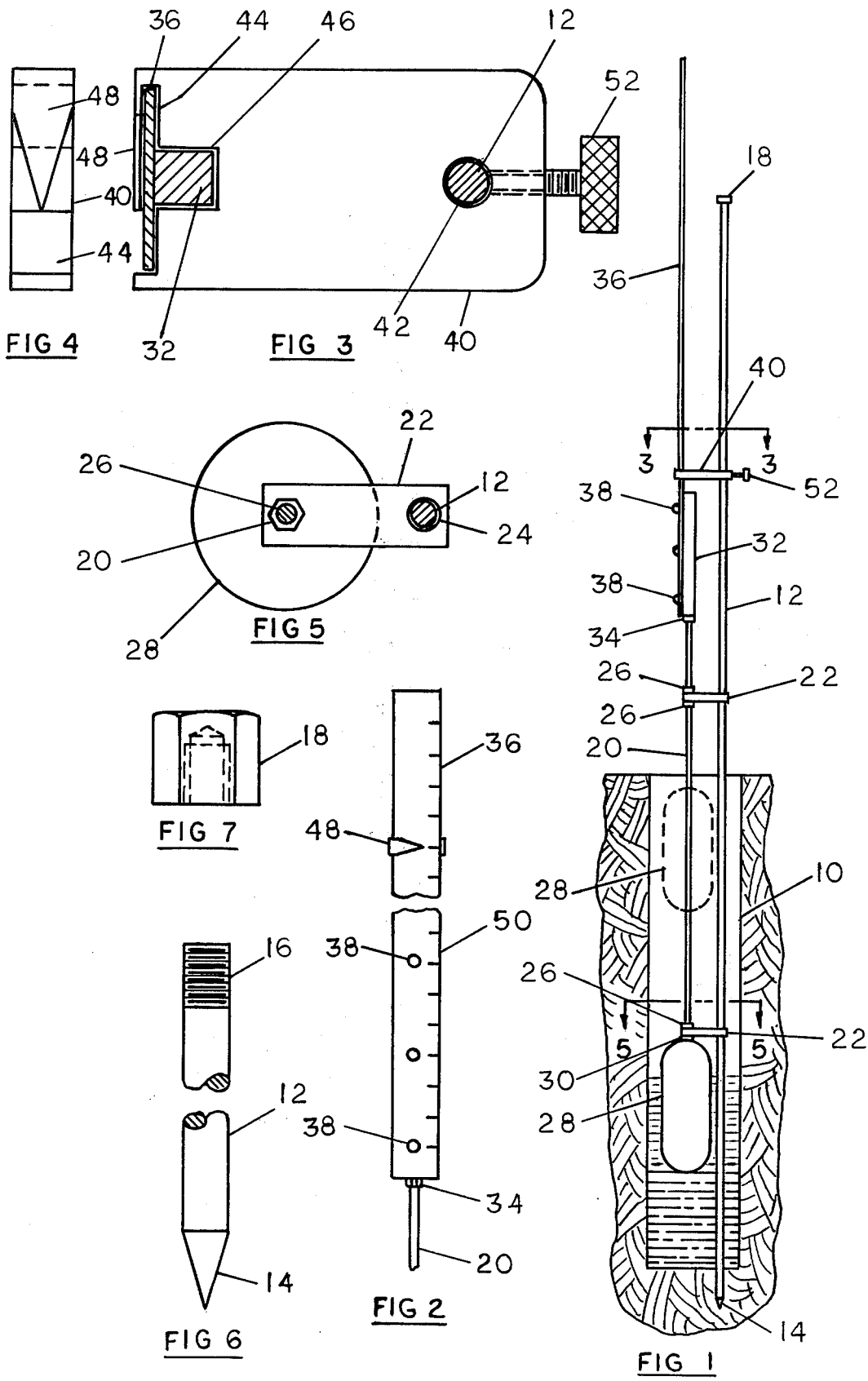

SOIL PERCOLATION TESTING APPARATUS

BACKGROUND OF THE INVENTION

The principal purpose of the present invention is to provide a very simple, yet sturdy testing apparatus to determine the percolation rate of soil. Prior devices have been devised heretofore for accomplishing similar purposes but these, in general, are more complex and, accordingly, more costly than the apparatus comprising the present invention. Two prior patents directly related to percolation testing comprise U.S. Pat. No. 3,892,126, to Curtin, dated July 1, 1975, and U.S. Pat. No. 3,945,247, to Anderson, dated Mar. 23, 1976. The Curtin patent adapts a conventional surveyor's tripod to the purpose of testing percolation rate by mounting a scale fixed at one end to a table top supported by the tripod and extending vertically therefrom in fixed manner for movement of the upper end of a float rod relative to the scale. The Anderson structure comprises a sophisticated housing which is lowered into the test hole and a gauge rod is movable within the housing and has the lower end upturned for purposes of observing the terminal surface of said upturned end relative to water level within the test hole, a timer being employed for indicating a test period, and another observation must be made at the end of said period relative to the upper surface of said upturned end of the gauge rod.

In contrast to the more complex structures of these two prior patents, U.S. Pat. No. 3,926,143, to Hothan, dated Dec. 16, 1975, discloses a device for use in determining the flow of water into a well, as distinguished from testing the percolation characteristics of the soil within which the well has been formed. A well casing precludes any contact of water in the well with the soil except through water inlet holes in the lower end of the well casing and the float moves a rod for observation of the upper end thereof above the upper end of the well casing, but no scale of any type is employed to determine measurements.

The present invention has been devised primarily to provide an extremely simple and thus, relatively inexpensive testing apparatus for determining percolation of soil, details of which are set forth below:

SUMMARY OF THE INVENTION

It is the primary object of the present invention to provide an extremely simple apparatus capable of being inexpensively manufactured for testing the percolation rate of water into soil by employing a simple elongated support rod having a pointed lower end adapted to be driven into the soil in the bottom of the test hole to constitute the sole support of the apparatus within the hole and a gauge rod having a float at the lower end thereof is slidable along the guide rod to move a light weight, elongated scale strip which is fixed to the upper end of the gauge rod and is movable by the float vertically relative to a reference indicator adjustably supported upon the upper portion of the guide rod.

It is another object of the invention to employ the reference indicator as a guide means for the scale strip, thereby minimizing the components of the apparatus.

A still further object of the invention is to provide a threaded cap on the upper end of the guide rod which may be employed in hammering the guide rod into the test hole.

Details of the foregoing objects and of the invention, as well as other object thereof, are set forth in the following specification and illustrated in the accompanying drawing, comprising a part thereof.

BRIEF DESCRIPTION OF THE DRAWING

FIG. 1 is a side elevation of the percolation testing apparatus comprising the present invention illustrated in operative position within an exemplary test hole shown in vertical section, the float of the apparatus being indicated in phantom in starting position and in full lines in an exemplary position it occupies at the end of a predetermined test period.

FIG. 2 is a fragmentary vertical elevation illustrating the upper portion of the gauge rod and a face view of the gauge strip which is connected to said gauge rod, said view also illustrating an exemplary position of a reference member which is supported by the guide rod.

FIG. 3 is a transverse sectional view showing on a larger scale than in FIGS. 1 and 2, details of the reference member as seen on the line 3—3 of FIG. 1.

FIG. 4 is a front end view of the reference member shown in FIG. 3, as seen on the line 4—4 thereof.

FIG. 5 is a transverse sectional view of the apparatus, as seen on the line 5—5 of FIG. 1, and illustrated on a larger scale than employed in said figure.

FIG. 6 is a foreshortened elevation showing on a larger scale than in FIGS. 1 and 2, details of the upper and lower ends of the guide rod.

FIG. 7 is a side elevation of a cap which is adapted to be threaded onto the upper end of the guide rod.

DETAILED DESCRIPTION

As indicated above, the present invention pertains to a percolation testing apparatus which is employed in relation to a soil testing hole 10 which is shown in exemplary manner in FIG. 1 in vertical section. In general common practice, a series of holes 10 are formed at various locations in an area of which the soil is to be tested. The holes may be formed in any suitable manner but usually by an appropriate boring apparatus. A practical dimension of such holes is approximately 6 inches in diameter and 36 inches in depth but, depending upon the particular type of soil, the diameter and depth of said holes may vary from the aforementioned examples. After mounting the apparatus described hereinafter within such holes, said holes are filled to a predetermined amount with water, a timing device, such as a stop watch, is started, and at the end of a predetermined test period, the depth of the water in the hole is measured in relation to a scale device included in the apparatus. Depending upon the rate of absorption, the soil is either approved or not approved for various types of use.

The testing apparatus comprising the present invention is very simple and practical for use and comprises an elongated guide or support rod 12 which, as shown best in FIG. 6, in foreshortened manner, has a pointed lower end 14 which is driven into the bottom of the test hole 10, as shown in exemplary manner in FIG. 1. In practical use, the guide rod 12 is about 6 feet in length and ⅜ or ½ inch in diameter but these dimensions are solely exemplary. The upper end 16 of the guide rod 12 preferably is threaded, as shown in FIG. 6, for mounting a cap 18 thereon, said cap being internally threaded for engagement with the end 16. The cap provides a ready means for hammering the upper end of the rod 12 incident to mounting the same within the test hole 10, the cap thereby preserving the upper end of the guide rod 12 for long use. Especially in view of the fact that the guide rod 12 is associated with water, a suitable material for forming the same is stainless steel but any other type of suitable metal or other material may be employed, if desired, within the spirit of the present invention.

An elongated gauge or float rod 20, which is of less length than the guide rod 12, is associated in use with said guide rod by means of at least one, and preferably a plurality of guide brackets 22 which, particularly for purposes of durability, are formed from a non-corroding metal, such as aluminum or otherwise. Referring to FIG. 5, one of the guide brackets 22 is shown in plan view and it will be seen that in one end thereof, a bearing hole 24 is formed for slidable engagement upon the guide rod 12. The opposite end of the bracket 22 has another hole formed therein through which the elongated gauge rod 20 extends. For simplicity of mounting the guide brackets 22 upon the gauge rod 20, the same is preferably threaded throughout its length and, for durability, the same is formed from stainless steel so as to resist corrosion. The purpose of threading the gauge rod 20 in such manner is in order that opposing lock nuts 26 may be threaded against the upper and lower surfaces of the guide brackets 22, and thereby fixedly position the guide brackets upon said rod in longitudinally spaced relationship to each other, one of said brackets 22 preferably being mounted adjacent the lower end thereof and the other one, substantially spaced longitudinally therefrom, all illustrated in exemplary manner in FIG. 1.

A suitable, preferably somewhat elongated float 28, formed from any appropriate corrosion-resistant material, such as either metal, plastic, or otherwise, is provided at its upper end with an internally threaded collar or boss 30, into which the lower end of gauge rod 20 is threaded, such as for purposes of not only connecting the float to the rod 20, but also affording an appropriate abutment for the lower guide bracket 22. From the foregoing, it will be seen that the guide brackets 22 provide ready means for guiding the elongated gauge rod 20 in parallel relationship to and along the guide rod 12, it being understood that the float and gauge rod 20 are of such dimension that they readily operate within the test hole 10 without interference with the sidewalls thereof.

In the initial position of the apparatus, the float 28 usually is located near the upper end of the hole 10, depending upon how much water is introduced to said hole for test purposes. Such an exemplary position is shown in phantom in FIG. 1, and after a predetermined period of time has elapsed, the float will be in a lower position, such as shown in full lines in FIG. 1, such relative positions being solely exemplary. For purposes of simplicity, the starting position of the apparatus described hereinafter, which is supported by the upper end of elongated gauge rod 20 is not illustrated in said initial position.

Connected to the upper end of elongated gauge rod 20 is a mount member 32 which also preferably is formed for corrosion-resistant material, such as aluminum or otherwise, and the lower end thereof is provided with a threaded socket into which the threaded upper end of gauge rod 20 is mounted, and such connection is completed by means of a lock nut 34. The purpose of the mount member 32 is to form a support for the lower end of an elongated, preferably light-weight and thin scale strip 36 which, for example, may be formed from relatively rigid stainless steel, and if desired, the same may be braced by being slightly arcuate in cross-section, similar to many types of coilable steel rules of well known type. The lower end of the scale strip 36 is firmly connected to the mount member 32 by means of a plurality of threaded, headed members 38, such as screws, which are received within tapped holes in the mount member 32. From the foregoing, it will be seen that the scale strip 36 moves vertically with the gauge rod 20 incident to the float 28, either descending within the test hole 10 during the testing operation or rising within said test hole as when the hole is being filled with water to a predetermined amount.

A reference bracket or member 40, which is best shown in detail in FIGS. 3 and 4, also is formed preferably from a corrosion-resistant material, such as aluminum or otherwise. At one end thereof as shown in FIG. 3, a hole 42 is formed through which the guide rod 12 extends. The opposite end of the member 40 is provided with a slot 44 in which the scale strip 36 is mounted for free sliding movement. Extending inward from the slot 44 is a space 46 within which the mount member 32 may be accommodated if it is necessary for the gauge rod 20 and scale strip 36 to move that high in use. Part of the front wall of the slot 44 comprises a reference marker 48, the outer end of which is pointed as clearly shown in FIG. 4, for purposes of being associated with the indicia 50 on the scale strip 36, as shown in exemplary manner in FIG. 2.

The reference member 40 is adjustably positionable upon the guide rod 12, especially for purposes of determining a suitable initial reading of the indicia 50 on the scale strip 36. Such initial adjusted position of member 40 upon the guide rod 12 is maintained by locking means, such as a headed screw 52, shown in exemplary manner in FIG. 3. It also will be seen that the reference member 40 serves the dual function of comprising a reference marker and also guide means for the vertically movable scale strip 36.

From the foregoing, it will be seen that the apparatus comprising the present invention is very simple and is formed of durable material, is capable of long life, as well as being easily and readily installed in suitable test holes, from which the apparatus readily is removable at the completion of testing operations.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

I claim:

1. Soil percolation testing apparatus comprising in combination, an elongated guide rod pointed at one end and adapted to be installed in a soil testing hole with the pointed end driven into the bottom of said hole for sole support thereby in said hole, a gauge rod of less length than said guide rod, at least one guide bracket secured to said gauge rod and provided with a bearing hole in which said guide rod extends for free sliding movement of said bracket longitudinally along said guide rod, a float secured to the lower end of said gauge rod below said guide bracket, an elongated scale strip secured to the upper end of said gauge rod, a reference bracket having an opening in one end to receive the upper portion of said guide rod for support by said rod, and also having a slot in the opposite end portion to accommodate said scale strip for free relative slide, locking means operable to secure said reference bracket adjustably on said guide rod, and a reference member on said reference bracket adjacent said slot therein and operable relative to said scale strip to indicate measuring indicia on said strip incident to testing the percolation rate of the soil in which said test hole is formed.

2. The apparatus according to claim 1 in which said reference member comprises part of said reference bracket and defines a part of one side of said slot in said bracket and has a pointed outer end, said member being parallel to said scale strip.

3. The apparatus according to claim 1 further including a cap threadably attached to the upper end of said guide rod and adapted to be hammered incident to installing the pointed end of said rod in the bottom of the test hole.

4. The apparatus according to claim 1 in which a pair of similar guide brackets are fixed to said gauge rod, one of said brackets being adjacent the float on the lower end of said rod and the other being in substantially spaced relation thereto toward the lower end of said scale strip.

5. The apparatus according to claim 1 further including an elongated mount member threadably connected at one end to the upper end of said gauge rod, and a plurality of tapped holes formed in spaced relation therein along one vertical face of said member for the reception of threaded headed members to attach the lower end of said scale strip fixedly to said gauge rod.

* * * * *